United States Patent
Laurberg

[19]
[11] Patent Number: 5,864,395
[45] Date of Patent: Jan. 26, 1999

[54] METHOD AND AN APPARATUS FOR IDENTIFYING FOREIGN BODIES IN PACKAGED BEVERAGES, AS WELL AS USE OF THE APPARATUS

[75] Inventor: Claus Kirkegaard Laurberg, Lyngby, Denmark

[73] Assignee: Kjaergaard Industri Automatic A/S, Losning, Denmark

[21] Appl. No.: 849,854

[22] PCT Filed: Dec. 12, 1995

[86] PCT No.: PCT/DK95/00504

§ 371 Date: Dec. 22, 1997

§ 102(e) Date: Dec. 22, 1997

[87] PCT Pub. No.: WO96/18883

PCT Pub. Date: Jun. 20, 1996

[30] Foreign Application Priority Data

Dec. 13, 1994 [DK] Denmark .................................. 1427/94

[51] Int. Cl.⁶ ..................................................... G01N 21/90
[52] U.S. Cl. ................... 356/239.6; 356/427; 250/223 B
[58] Field of Search ..................................... 356/240, 239, 356/426, 427, 428; 250/223 B, 234, 235, 236

[56] References Cited

U.S. PATENT DOCUMENTS

| | | | |
|---|---|---|---|
| 4,209,802 | 6/1980 | Fogg et al. ............................... | 356/427 |
| 4,241,256 | 12/1980 | Tagaya et al. ........................... | 250/223 |
| 4,367,405 | 1/1983 | Ford ........................................ | 250/223 B |
| 4,402,612 | 9/1983 | Alexander et al. ..................... | 356/240 |
| 5,072,108 | 12/1991 | Ishikawa ................................. | 250/223 B |
| 5,444,237 | 8/1995 | Takizawa ................................ | 356/240 |

FOREIGN PATENT DOCUMENTS

| | | | |
|---|---|---|---|
| 0186278 | 2/1986 | European Pat. Off. ....... | G01N 21/90 |

*Primary Examiner*—Hoa Q. Pham
*Attorney, Agent, or Firm*—Klein & Szekeres, LLP

[57] ABSTRACT

A method and an apparatus for identifying foreign bodies in packaged beverages are employed where the package and the beverage are translucent and the foreign bodies have a density greater than that of the beverage. A novel aspect of the method is that the package is oriented in a first position in which the foreign bodies are collected on an internal, upwardly directed face in the package, and the package is then turned to at least one subsequent inclined position having an inclination sufficient for the foreign bodies to perform a downward movement along said face. During this movement, at least one of the foreign bodies is identified by comparing at least two successive position-determining detections. This provides a method and an apparatus for certain identification of foreign bodies in dark as well as light beverages, and in disposable as well as recyclable packages.

15 Claims, 4 Drawing Sheets

METHOD AND AN APPARATUS FOR IDENTIFYING FOREIGN BODIES IN PACKAGED BEVERAGES, AS WELL AS USE OF THE APPARATUS

FEDERALLY SPONSORED RESEARCH OR DEVELOPMENT

Not Applicable

CROSS REFERENCE TO RELATED APPLICATIONS

Not Applicable

BACKGROUND OF THE INVENTION

1. Field of the Invention

The present invention concerns a method of identifying foreign bodies in packaged beverages, where the package and the beverage are translucent, and the foreign bodies have a density greater than that of the beverage. The invention moreover concerns devices for performing the method and uses of said devices.

2. Description of the Related Art

Methods of this type are known. In the performance of these known methods, the foreign bodies are identified manually in that an operator manually turns the package, while observing whether foreign bodies move in the beverage. These known methods are not useful for identification of small foreign bodies, such as glass splinters, since they are frequently very difficult to observe. Further, it is not possible to identify foreign bodies with certainty in dark beverages owing to poor translucency. Finally, it has been found in practice that a large batch of beverages has to be rejected each time foreign bodies are observed in these. The reason is that the manual identification is performed only once an hour, and that it is desired not to place doubtful beverages with impurities on the market. Thus, the method is very expensive in the event that foreign bodies are observed in the beverages.

FR 2 607 589 discloses a method and a system for automatic identification of foreign bodies in glass bottles, in particular champagne bottles. The foreign bodies are detected using a spot scanner, while the bottle is turned about a vertical and a horizontal axis. However, this method does not enable the foreign bodies to be distinguished from carbonic acid and air bubbles, for which reason the method has been found to be unuseful in practice. Furthermore, the method cannot be applied to dark liquids at all.

Further, U.S. Pat. No. 5,072,108 discloses a method wherein the bottle to be inspected is rotated rapidly and is photographed durig the rotation. Scratches in the surface of the bottle will hereby be imaged as horizontal lines, while the foreign bodies in the non-rotating liquid can easily be identified. However, this method cannot be used for dark liquids either. It may likewise be a problem to detect foreign bodies at the domed bottom of the bottle.

SUMMARY OF THE INVENTION

The object of the invention is to provide a method of the type mentioned in the opening paragraph, wherein reliable identification of foreign bodies, in particular glass splinters, can be performed in both dark and light beverages. The method must be capable of identifying foreign bodies in both disposable packages and recyclable packages in which scratches, flaws, etc. frequently occur. Another object of the invention is to provide an apparatus for performing the method and to define uses of the apparatus.

The method of the invention is characterized in that the package is oriented in a first position in which the foreign bodies are collected on an internal, upwardly directed face in the package, and the package is then turned to at least one subsequent inclined position which has an inclination sufficient for the foreign bodies to perform a downward movement along said face, during which at least one of these is identified by comparison of at least two successive position-determining detections. As a result, the method provides certain identification of foreign bodies having a density greater than that of the beverage in all types of translucent beverages.

To identify foreign bodies, e.g. glass splinters, in packaged beverages, the package is first oriented in a position in which the foreign bodies are collected on an internal, upwardly directed face in the package. The package is then turned to at least one subsequent inclined position, so that the foreign bodies perform a downward movement along the face. Simultaneously with or immediately after the turning, at least two position-determining detections of the packaged beverage are performed, during which any present foreign body which moves downwards is identified by comparison of the two detections.

Further, all other foreign bodies having a density lower than that of the beverage, such as carbonic acid bubbles and other ingredients in the beverage, will move upwards with certainty, i.e. in a direction opposite to that of the foreign bodies which are to be detected, and even in liquid layers above these foreign bodies so that the movement of these other foreign bodies do not interfere with either the movement or the detection of the foreign bodies whose presence in the liquid is to be revealed.

Moreover, the foreign bodies to be revealed are collected and move within a well-defined region, viz. on the inner side of the upwardly directed face, so that they are gathered and easy to detect.

Expedient embodiments of the invention are described below.

The size of the foreign bodies may be detected, thereby providing a more reliable detection and identification of any present foreign body. Further, it is possible to put a limit to the size of foreign bodies that are accepted in the comparison with predetermined values.

The detections may be performed in the same direction toward the package face. This obviates the necessity of taking the orientation of the package into consideration in the subsequent comparison of the detections.

In another expedient embodiment, the detections are performed in a direction substantially at right angles to the package face. This ensures good imaging of the foreign bodies which move along the inner side of the package.

The invention moreover comprises an apparatus for identifying foreign bodies in a packaged beverage, wherein the package and the beverage are translucent, the foreign bodies having a density greater than that of the beverage, the apparatus comprising (a) orienting means for orienting the package in a first position wherein the foreign bodies are collected on an internal, upwardly-directed face in the package, and for subsequently orienting the package in at least one inclined position having an inclination sufficient for the foreign bodies to perform a downward movement along the upwardly-directed face; (b) detecting means for performing position-determining detections of the foreign bodies; and (c) identification means for identifying the foreign bodies by the comparison of at least two successive position-determining detections. As a result, the apparatus can automatically perform identification of foreign bodies.

In a particularly expedient embodiment of the apparatus, the apparatus comprises a package holder which is fixed with respect to the detecting means with a view to stationary identification, e.g. with respect to a passing transport column of packages from which a package is periodically taken out for control. This ensures that impurities, flaws, scratches, etc. in the package are not identified as foreign bodies, since flaws, etc. will not be registered as moving bodies in the subsequent comparison of the detection. This is a great advantage in the identification of foreign bodies in recycled bottles which almost always contain scratches, etc.

In another expedient embodiment of the apparatus, the apparatus comprises support means which are adapted to support the packages during their transport, e.g. in a bottle column, with a view to continuous identification. It will hereby be possible to perform identification of foreign bodies without removing the package from the bottle column. It will hereby be possible to check many bottles automatically within a short period of time.

The detecting means may advantageously be formed by one or more CCD cameras, since this enables automatic comparison of the detections via a computer. Furthermore, the CCD camera has a broad wavelength range, which makes it possible to register e.g. red and infrared light.

A light source may be provided behind the package in alignment with the packaged beverage and each sensor. This ensures good imaging of any foreign bodies.

In a particularly expedient embodiment of the invention, the light source emits light having a wavelength of between 600 and 900 nm. It is hereby possible to identify foreign bodies in even dark beverages.

The invention also comprises a use of said apparatus for identification of foreign bodies in beverages which are packaged in glass bottles. It is hereby possible to identify foreign bodies in e.g. beer, soft drink, wine and medicine glass bottles.

The invention also comprises a use of said apparatus for identification of foreign bodies in beverages which are packaged in plastics bottles. It is hereby possible to identify foreign bodies in e.g. beer, soft drink, wine and medicine plastics bottles.

BRIEF DESCRIPTION OF THE DRAWINGS

The invention will be explained more fully below with reference to the drawing, in which FIG. 1 schematically shows a bottle arranged in a first position.

DETAILED DESCRIPTION OF THE INVENTION

Figure 1:
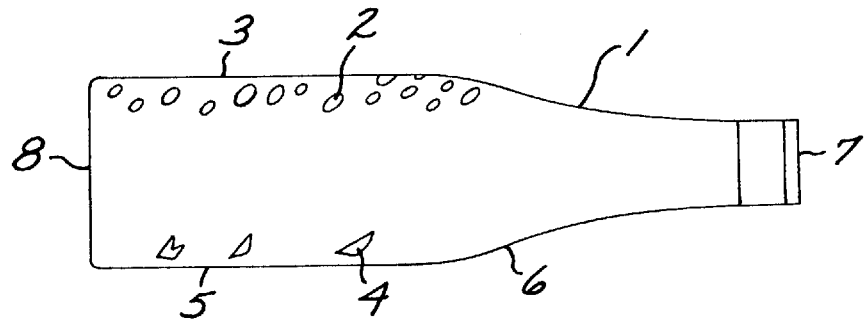

FIG. 1 shows a section in a beer bottle 1 which is arranged in a first substantially horizontal position, in which air and carbonic acid bubbles 2 as well as other foreign bodies having a density smaller than that of the beverage are collected in the liquid at the internal, downwardly directed face 3 of the bottle, and in which foreign bodies 4 in the form of glass splinters are collected along the internal, upwardly directed face 5 of the bottle.

Figure 2:
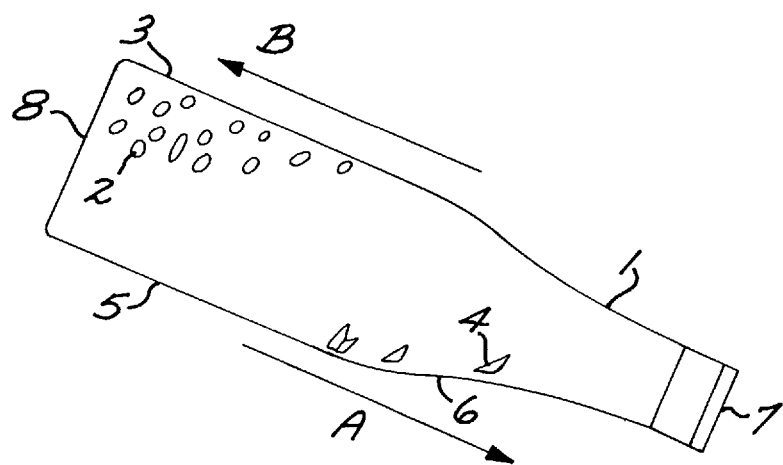
FIG. 2 shows the same arranged in a second position, in which the glass splinters move downward and air bubbles move upwards.

The bottle 1 is then turned to at least one subsequent inclined position, one of which being shown in FIG. 2. The shown inclined position has an inclination sufficient for the foreign bodies 4 to perform a downward movement along the internal, upwardly directed face 5 of the bottle, as shown by the arrow A. Air and carbonic acid bubbles 2 move upwards in the liquid and then along the internal, downwardly directed face 3 of the bottle in the opposite upward direction, as shown by the arrow B.

Figure 5:
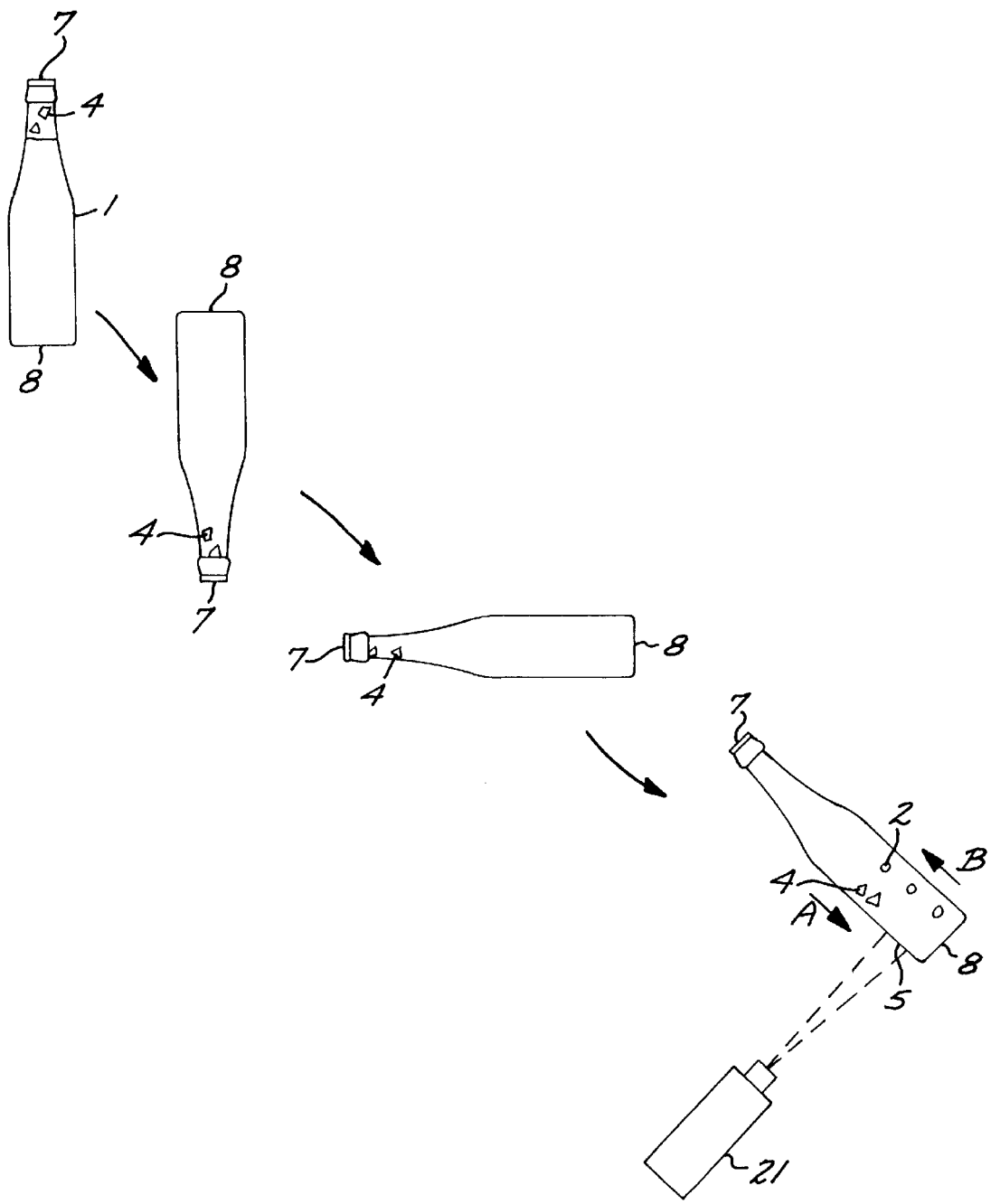
FIG. 5 shows a bottle in four different positions according to an embodiment of the method.

Then a plurality of position- and size-determining detections are performed at the internal, upwardly directed face 5 of the bottle. The detections may advantageously be performed in an area around the constriction 6 of the bottle, but might also be performed at e.g. the mouth 7 or bottom 8 of the bottle, as shown in FIG. 5. This figure moveover shows that the bottle may be turned 180° in the turning movement. This may be particularly advantageous, if the bottle contains a liquid which tends to form very dense foam. Such a case involves the risk that any foreign bodies 4, if any, may be caught in the foam and therefore are not present on the upwardly directed face 5 in the bottle in the starting position. When the bottle 1 is turned 180°, foreign bodies, if any, will drop down into the liquid and settle on the upwardly directed face 5, in this case at the opening 7 of the bottle. The turning movement may then be continued until the detecting position is reached.

Then at least two successive position- and size-determining detections are compared, and at least one of the foreign bodies 4 is identified.

Detections are performed in a particularly advantageous embodiment of the invention in a direction substantially at right angles to the package face, so that the comparison of the detections only reveals differences that are caused by foreign bodies 4 and thus not impurities, flaws, etc. in the package itself.

The invention also concerns an apparatus for performing the method. The apparatus comprises orienting means for orienting the package in a first position in which the foreign bodies are collected on an internal, upwardly directed face in the package, and then orienting the package in at least one subsequent inclined position which has an inclination sufficient for the foreign bodies 4 to perform a downward movement along said face. The apparatus moreover comprises detecting means which are adapted to perform position-determining detections of the foreign bodies 4 as well as means for identifying the foreign bodies 4 by comparison of at least two successive position-determining detections.

Figure 3:
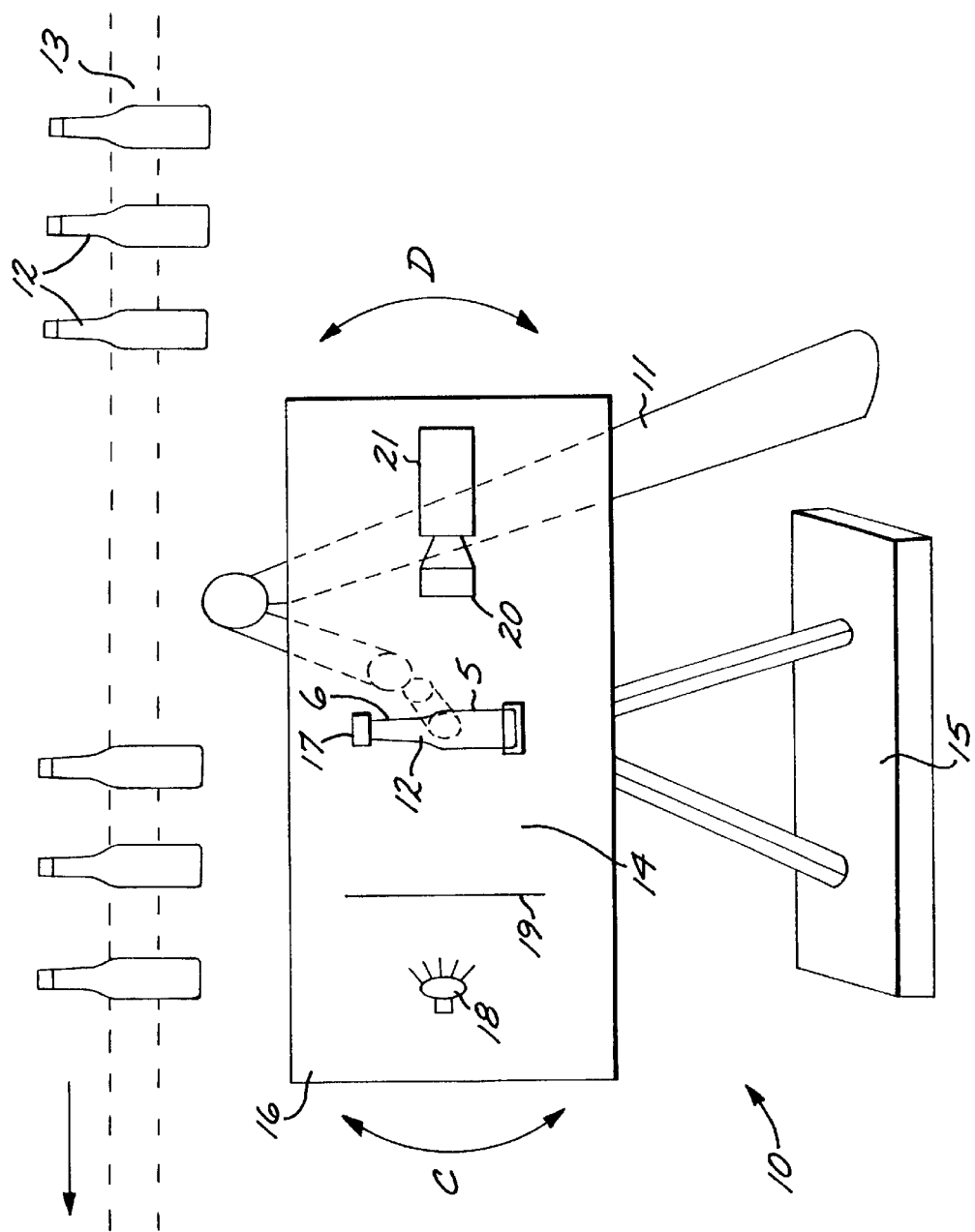
FIG. 3 shows an embodiment of an apparatus for performing the method in connection with spot tests.

FIG. 3 shows an apparatus for identifying foreign bodies 4 in connection with spot tests of beer and soft drink bottles in a bottle column.

A robot arm 11 is arranged at the side of the apparatus 10, said robot arm 11 being adapted to take out bottles 12 from a bottle column 13 and to place them in the apparatus 10, and vice versa. This handling of bottles might also take place manually.

The apparatus 10 comprises orienting means 14 which are suspended from a structure 15 which stands on the floor in the immediate vicinity of the bottle column 13. The orienting means 14 comprise a motor (not shown) from which a frame 16 having a substantially centrally located bottle holder 17 is suspended.

In succession, the frame 16 moreover accommodates a light source 18, a diffuser 19, a lens having an optical filter 20 and a detecting means 21. All these elements will thus rotate and be mutually fixed, as shown by the arrows C and D, when the motor is activated.

The light source 18, which is arranged at one end of the frame, emits light having a wavelength of about 600–900 nm, thereby making it possible to identify foreign bodies 4 in dark beverages.

A diffuser 19 is arranged in front of the light source 18 and diffuses light from the light source 18, thereby providing even illumination from the light source 18.

In the shown embodiment, the detecting means is formed by a CCD camera 21 in front of which the lens having the optical filter 20 is positioned. The CCD camera 21 focuses on an area around the constriction 6 of the bottle having an extent of about 3×3 cm and a depth of about 0–5 mm from the internal, upwardly directed face 5 of the bottle. The detections might also be performed at another location along the face of the bottle, provided that the foreign bodies 4 can perform a downward movement upon turning. The CCD camera 21 and the lens having the optical filter 20 might advantageously also be built together.

The CCD camera 21 is connected to a computer (not shown) which performs a comparison of the detections and then identifies any present foreign bodies 4. When identifying foreign bodies 4, the computer provides a signal to this effect so that the necessary actions can be performed. The computer may advantageously be coupled to a monitor, and in another embodiment the comparison might take place manually via the monitor.

In the use of the apparatus 10, the robot arm 11 takes out a bottle 12 from a bottle column 13 and places the bottle 12 in the bottle holder 17 which holds the bottle 12.

Then the motor performs a first rotation of the frame 16 and the parts attached to it (light source 18, diffuser 19, bottle holder 17, bottle 12, lens with optical filter 20 and CCD camera 21), so that the bottle 12 is placed in a substantially horizontal position. If the bottle holder 17 is horizontal in the starting position, it is not necessary to rotate the frame 16, of course. The frame 16 is maintained in this position for about 1–10 sec., so that any present foreign bodies 4 are collected along the internal, upwardly directed face 5 of the bottle, as essentially shown in schematic form in FIG. 1.

Then the second rotation is initiated, during which the motor rotates the frame 16 and the parts 18, 19, 17, 12, 20, 21 attached to it, with the simultaneous performance of a plurality of position- and size-determining detections, e.g. at the constriction 6 of the bottle, as essentially shown in schematic form in FIG. 2. The detections are compared in the computer which applies a signal when identifying foreign bodies 4. It is noted that the rotation may be stepwise, if desired, and that the angle of the rotation depends on the bottle type, the size of the foreign bodies, etc.

When the identification has been completed, the robot arm 11 takes out the bottle 12 from the bottle holder 17, and a new identification sequence may be initiated.

Figure 4:
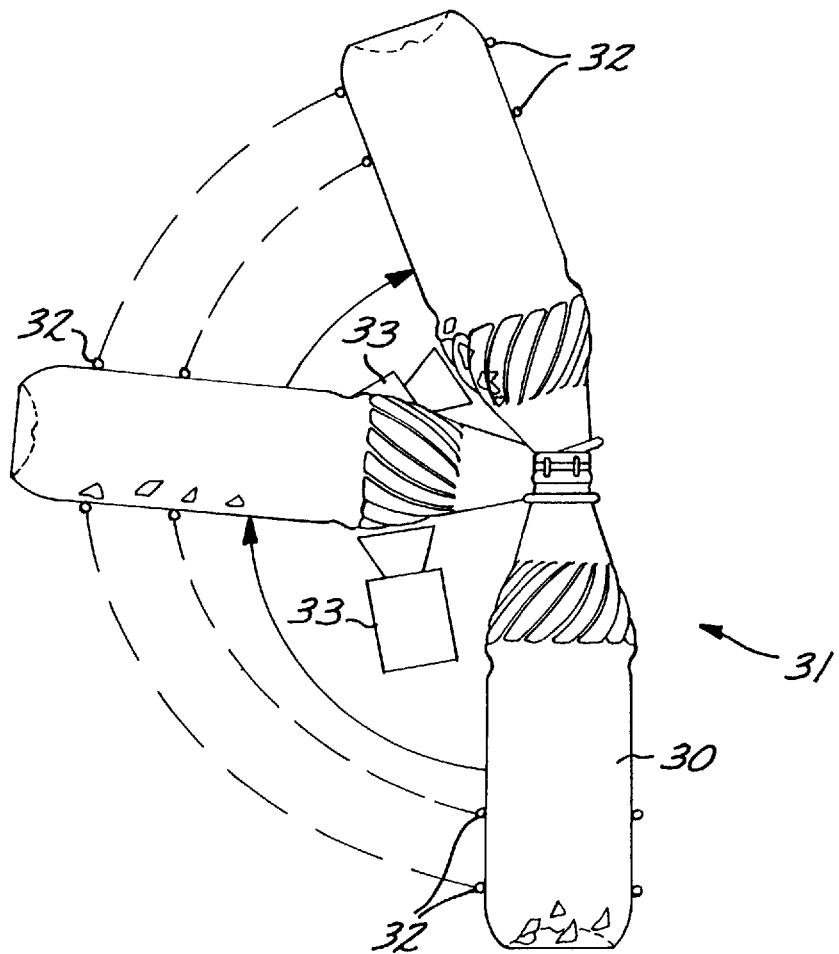
FIG. 4 is a schematic end view of another embodiment of an apparatus for performing the method.

FIG. 4 is a schematic end view of a plastics bottle 30 which performs a turning movement in another embodiment of an apparatus 31 for identification of foreign bodies 4 in beverages. The apparatus 31 is adapted to be used in connection with continuous identification of foreign bodies in a bottle column during the transport of the bottle 30 in the bottle column. It is noted that the apparatus 31 may also be used for other types of packages than plastics bottles. The distinctions from the above apparatus 10 are described below.

The orienting means of the apparatus 31 comprise support means 32 which are arranged along the sides of the bottle 30, and which are adapted to support the bottle 30 in several positions along a bottle column. It is shown in FIG. 4 from the end how the bottle 30 in a bottle column will turn, as the support means 32 move the bottle 30 to this position in the column, while the bottle 30 is being fed by feeding means (not shown).

In an advantageous embodiment of the apparatus, the detecting means comprise a CCD camera 33 which follows the bottle 30 in the bottle column, as shown in FIG. 4. It is thus ensured that the detections are performed in the same direction toward the bottle face, and in a particularly advantageous embodiment they are performed at right angles to the bottle face.

In another advantageous embodiment of the invention (not shown), the detecting means comprise several CCD cameras which are arranged stationarily along the bottle column. The CCD cameras are thus fixed, but the detections are performed in the same direction toward the bottle face.

In the use of the apparatus shown in FIG. 4, the bottles are turned automatically, as the support means 32, which are arranged all the way along the bottle column, move the bottle 30 up to the necessary positions. Simultaneously, a plurality of detections are performed with one or more cameras, and these are compared and any foreign bodies are identified in the same manner as described above.

As shown in FIGS. 3 and 4, the apparatus may be used in particular for identification of glass and plastics splinters in glass and plastics bottles (including PET bottles) in connection with the bottling of beer and soft drinks. The apparatus may also be employed for identification of other foreign bodies in e.g. medicine bottles, vials, jars, glass, wine bottles, etc., provided the package and the beverage are translucent and the foreign bodies have a density greater than that of the beverage.

In an embodiment of the apparatus of the invention (not shown), the detecting means are secured to the robot arm, and the robot arm is adapted to perform orientation of the package. The orienting means are thus formed by the robot arm, and it will not be necessary to place the package in an independent apparatus.

Many modifications can be made within the scope of the invention without departing from the idea of the invention.

Infrared light having a wavelength of about 600–900 nm is used in the embodiment shown, but this is not any restriction since other wavelengths may be used, provided they are within the detecting range of the detecting means. For CCD cameras, the sensitive wavelength range is thus about 300–1000 nm, so that all types of light having this wavelength can be used.

What is claimed is:

1. A method of identifying foreign bodies in a packaged beverage, wherein the package and the beverage are translucent, said foreign bodies having a density greater than that of the beverage, said method comprising the steps of:

orienting the package in a first position in which said foreign bodies are collected on an internal, upwardly directed face in the package;

subsequently turning the package to at least one inclined position having an inclination sufficient for said foreign bodies to perform a downward movement along said face;

performing at least two successive position-determining detections during said downward movement; and identifying at least one of the foreign bodies by performing a comparison of said successive position-determining detections.

2. The method according to claim 1, further comprising the step of detecting the size of said at least one identified foreign body and comparing said size with predetermined values.

3. The method according to claim 1, wherein the position-determining detections are performed in the same direction toward the package face.

4. The method according to claim 3, wherein the position-determining detections are performed in a direction substantially at right angles to the package face.

5. An apparatus for identification of foreign bodies in a packaged beverage, wherein the package and the beverage are translucent, said foreign bodies having a density greater than that of the beverage, said apparatus comprising:

orienting means for orienting the package in a first position wherein the foreign bodies are collected on an internal, upwardly directed face in said package and for subsequently orienting said package in at least one inclined position having an inclination sufficient for said foreign bodies to perform a downward movement along said face;

detecting means for performing position-determining detections of said foreign bodies; and identification means for identifying the foreign bodies by comparison of at least two successive position-determining detections.

6. The apparatus according to claim 5, wherein the orienting means comprise a separate package holder which is fixedly connected with said detecting means with a view to stationary identification.

7. The apparatus according to claim 6, wherein said package holder and said detecting means fixedly connected with said package holder are tunably suspended as a unitary assembly.

8. The apparatus according to claim 5, wherein the orienting means comprise support means for supporting the package during its transport in a package column with a view to continuous identification.

9. The apparatus according to claim 8, wherein said detecting means are formed by at least two units arranged at two different, stationary positions along said package column.

10. The apparatus according to claim 8, wherein the detecting means, during detection, are adapted to follow the package concerned during its transport in the package column.

11. The apparatus according to claim 5, wherein the detecting means comprise a CCD camera.

12. The apparatus according to claim 5, wherein a light source is provided behind said package in alignment with said packaged beverage and each detecting means.

13. The apparatus according to claim 5, wherein said light source emits light having a wavelength of between 600 nm and 900 nm.

14. The use of an apparatus according to claim 5 for identification of foreign bodies in beverages packaged in glass bottles.

15. The use of an apparatus according to claim 5 for identification of foreign bodies in beverages packaged in plastic bottles.

* * * * *